United States Patent
Green

(10) Patent No.: US 9,844,317 B2
(45) Date of Patent: Dec. 19, 2017

(54) METHOD AND SYSTEM FOR AUTOMATIC EYESIGHT DIAGNOSIS

(71) Applicant: GREEN C.TECH LTD, Even Yehuda (IL)

(72) Inventor: Michal Green, Even Yehuda (IL)

(73) Assignee: GREEN C.TECH LTD, Even Yehuda (IL)

( * ) Notice: Subject to any disclaimer, the term of this patent is extended or adjusted under 35 U.S.C. 154(b) by 0 days.

(21) Appl. No.: 15/653,564

(22) Filed: Jul. 19, 2017

(65) Prior Publication Data
US 2017/0311793 A1 Nov. 2, 2017

Related U.S. Application Data

(63) Continuation of application No. PCT/IL2016/050066, filed on Jan. 20, 2016.

(60) Provisional application No. 62/105,235, filed on Jan. 20, 2015.

(51) Int. Cl.
*A61B 3/113* (2006.01)
*A61B 3/00* (2006.01)
*A61B 3/032* (2006.01)

(52) U.S. Cl.
CPC ............. *A61B 3/005* (2013.01); *A61B 3/032* (2013.01); *A61B 3/113* (2013.01)

(58) Field of Classification Search
CPC ....... A61B 3/113; A61B 3/102; A61B 3/0008; A61B 3/14
USPC ..................... 351/209, 210, 211, 246, 45, 46
See application file for complete search history.

(56) References Cited

U.S. PATENT DOCUMENTS

| 5,026,151 | A | 6/1991 | Waltuck et al. | |
| 5,070,883 | A | 12/1991 | Kasahara | |
| 5,264,877 | A | 11/1993 | Hussey | |
| 6,511,175 | B2 | 1/2003 | Hay et al. | |
| 7,480,396 | B2 | 1/2009 | Teiwes et al. | |
| 8,845,099 | B2 | 9/2014 | Clopton | |
| 2002/0118339 | A1* | 8/2002 | Lowe | A61B 3/032 351/209 |
| 2012/0293773 | A1 | 11/2012 | Publicover et al. | |

OTHER PUBLICATIONS

International Search Report of PCT Application No. PCT/IL2016/050066 dated May 5, 2016.

* cited by examiner

*Primary Examiner* — Hung Dang
(74) *Attorney, Agent, or Firm* — Pearl Cohen Zedek Latzer Baratz LLP

(57) ABSTRACT

A system for eyesight diagnosis may include a vision test unit and a controller. The vision test unit may include at least one eye movement tracking unit configured to track the movement of a portion of the eye, at least one screen for visual stimulation and a shuttering unit configured to controllably block the field of view (FOV) of each eye separately. The controller may be configured to: display to a patient a first visual stimulation on the at least one screen, cause the shuttering unit to block the FOV of a first eye of the patient while unblocking the FOV of a second eye, receive a first signal indicative of the second eye movement of the patient from the at least one eye movement tracking unit and diagnose the patient's eyesight based on the received first signal.

20 Claims, 6 Drawing Sheets

METHOD AND SYSTEM FOR AUTOMATIC EYESIGHT DIAGNOSIS

CROSS REFERENCE TO RELATED APPLICATIONS

This application is a continuation of PCT International Application No. PCT/IL2016/050066, International Filing Date Jan. 20, 2016, claiming the benefit of U.S. Patent Application No. 62/105,235, filed Jan. 20, 2015, all of which are hereby incorporated by reference.

BACKGROUND OF THE INVENTION

Visual Acuity (VA) tests in humans are usually performed by professionals such as ophthalmologists, optometrists and in some cases public-health nurses. Such tests require special training, special equipment and the patient's collaboration.

In a typical VA test the professional preforming the test presents visual stimulations such as presenting objects or characters (e.g. numbers and letters) at various sizes presented to the patient at decreasing size order. The patient is required to respond to the presented visual stimulation by identifying, verbally or in any other way (e.g., hand waving) the presented object or character. The professional tests each of the patient's eyes separately, while covering the other eye and the patient verbally required to notice the professional whether he/she sees the visual stimulation presented. A manual actuality test conducted by an optometrist that requires the patient's active participation takes more than 10 minutes and its accuracy relays heavily on the response of the patient and the professionalism of the optometrist.

Similar approach is implemented when testing a three-dimensional (3D) vision of the patient. The patient is given polarizing glasses and presented with a 3D visual stimulation. Here again the professional needs to hear the verbal response of the patient to various 3D visual stimulations in order to detect problems with the patient's 3D vision.

Tests that require a full verbal collaboration of the patient cannot be used to test or inspect infants, babies and people having difficulties in verbal communication such as people suffering from autism. The only known method of conducting VA tests in these groups is the use of Teller-Cards (also known as Teller Visual Acuity Cards). Teller cards are cards presenting vertical (or horizontal) black- and white strips at different widths and frequencies, starting at relatively wide stripes and ending with relatively narrow strips. Specially trained ophthalmologist tracts the eye movement of the patient using a small lamp as the patient is presented with the various Teller-cards. Each Teller card includes alternating black and white strips (either rows or columns) having a known/constant width alternating at a specific frequency. The Teller cards are presented to the patient in a contrast decreasing order starting with a card having wide strips and low frequency. When a patient cannot detect the contrast between the white and black strips (i.e., the card will look as a solid grey square), the professional conducting the test may notice a change in the concentration or gazing of the patient, indicating that the patient didn't notice the contrast presented. Teller cards are defined by a number of Cycles Per Centimeter (CPC) from the first strip to the last strip, presented at each cards. There are cards having 0.23, 0.32, 0.43, 0.64, 0.86, 1.3, 1.6, 2.4, 3.2, 4.8, 6.5, 9.8, 13.0, 19.0, 26.0 CPC, wherein, the 0.23 CPC has the widest strips and the 26.0 CPC has the narrowest strips. An eye of a patient having the ability to see the highest Teller card having 26.0 CPC has 6/6 vision (e.g., that at six meters test distance the patient could correctly identify a letter that a 'normal' sighted person should see at six meters, also referred to as normal vision). However, since the testing is done to both eyes simultaneously, the test can only give an indication that the patient may have a vision acuity problem. Some exemplary Teller-cards are illustrated in FIGS. 1A-1D.

Prior art methods for testing eyesight require the use of dilating eye drops that contain medication to enlarge (dilate) the pupil of the eye. There are two types of drops: one type stimulates contraction of the muscles that enlarge the pupil (such as phenylephrine); the other type relaxes the muscles that make the pupil constrict and also relaxes the muscle that focus the lens of the eye (such as cyclopentolate). The use of such dilating eye drops is very unpleasant and leaves the patient with blurred eyesight for couple of hours after the test.

Currently there is no reliable objective method or system for conducting acuity tests or diagnosing eyesight in general that does not relay on the patient's collaboration.

SUMMARY

Embodiments of the invention may be related to a method and a system for eyesight diagnosis. The system may include a vision test unit and a controller. The vision test unit may include at least one eye movement tracking unit that may be configured to track the movement of a portion of the eye, at least one screen for visual stimulation and a shuttering unit that may be configured to controllably block the field of view (FOV) of each eye separately. In some embodiments, the controller may include a processor and a non-volatile memory that store thereon instructions that when executed by the processor may cause the controller to: display to a patient a first visual stimulation on the at least one screen, cause the shuttering unit to block the FOV of a first eye of the patient while unblocking the FOV of a second eye, receive a first signal indicative of the second eye movement of the patient from the at least one eye movement tracking unit and diagnose the patient's eyesight based on the received first signal.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate,

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Embodiments of the present invention may be related to providing a system and method for conducting reliable tests for eyesight diagnosis (e.g., acuity test, squint detection tests, 3D vision tests etc.). In some embodiments, using a method and a system of the invention may not require any cooperation or collaboration from a testee (e.g., a human patient been tested). Such a system may be used for testing the eyesight of infants, babies, any other patient. A system according to embodiments of the invention may rely on objective, substantially accurate measurements done automatically by a computerized controllable system.

A system according to some embodiments of the invention may not rely on receiving inputs from humans, either from a professional conducting the test or the patient. The system may receive substantially accurate measurements from sensors (such as, infra-red (IR) cameras or electrodes) and information from other controllable components (e.g., a shuttering unit that blocks the FOV of an eye) included in the system. Accordingly, since human interference is not required the test may be conducted at a very short time, for example, in less than 2 minutes or even less than 80 seconds An exemplary system according to embodiments of the invention may detect the eye movement using infrared (IR) sensors. The eye movement may be caused by a controllable visual stimulation displayed to the patient on a screen, for example, a Teller card. The system may further include a wearable device, such as, for example, special glasses, that enables controllable blocking of the Field Of View (FOV) of each eye separately. The IR sensor may be either located on the wearable device (e.g. glasses) or located at a predetermined distance from the patient's eyes, for example, near the screen presenting the visual stimuli.

Figure 1A:
FIGS. 1A, 1B, 1C and 1D are exemplary prior art Teller cards.
Figure 1B:
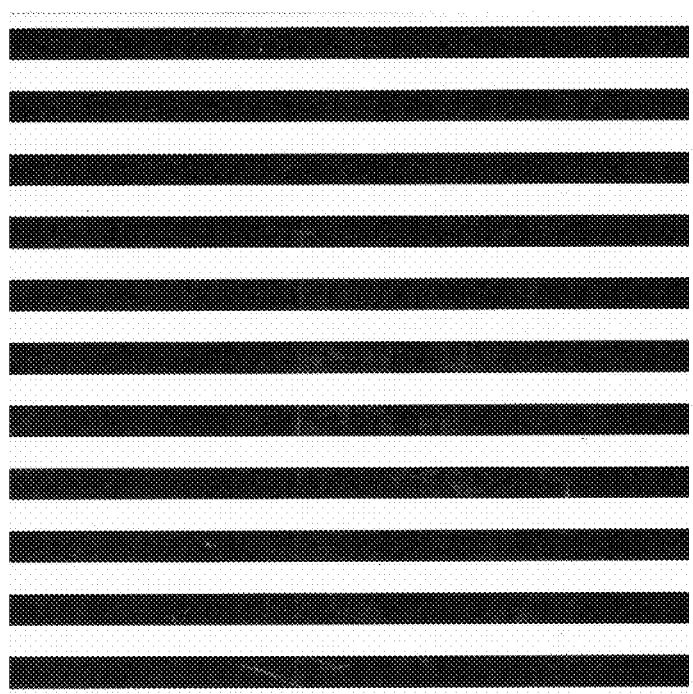
Figure 1C:
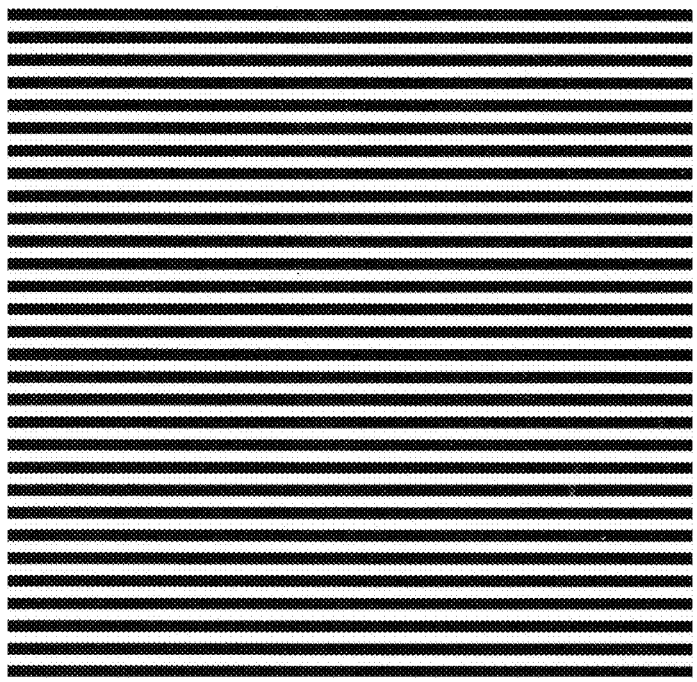
Figure 1D:
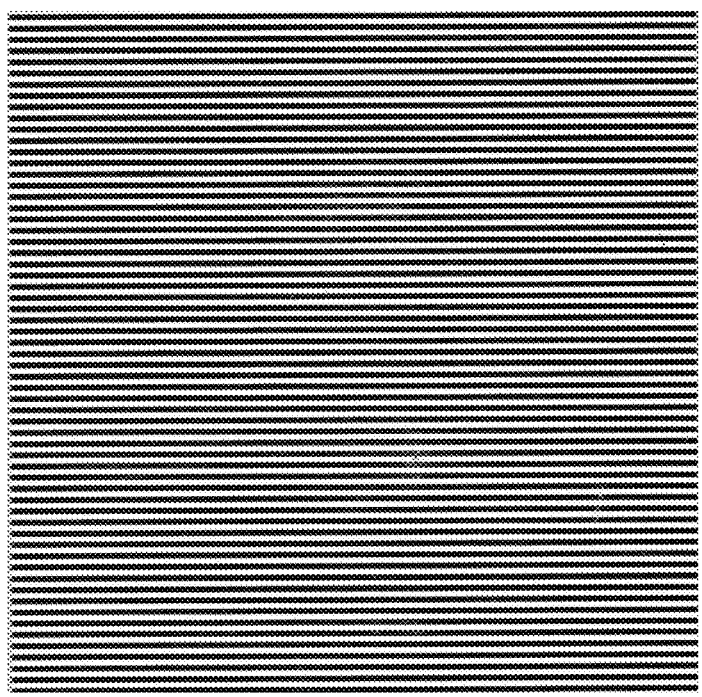
Figure 2:
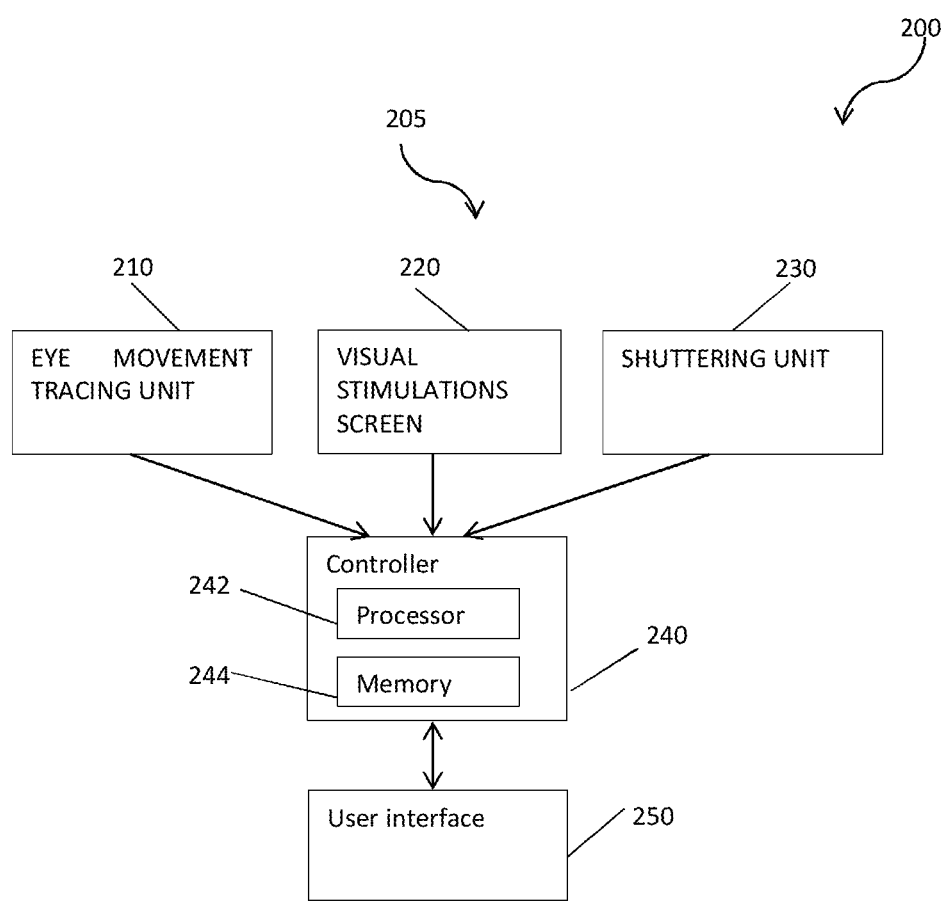
FIG. 2 is a block diagram of a system for eyesight diagnosis according to some embodiments of the invention.

Reference is made to FIG. 2 that is a block diagram of a system for automatic eyesight diagnosis according to some embodiments of the invention. System 200 may also be suitable for detecting several deviations from healthy eye sight, such as, acuity, 3D sight problems, squint or the like. System 200 may include a vision test unit 205 and a controller 240. Vision test unit 205 may include at least one eye movement tracking unit 210 configured to track the movement of a portion of the eye (e.g., the pupil, the iris, the muscles of the eye, or the like), at least one visual output device, such as screen 220 for visual stimulation, and shuttering unit 230 that may be configured to controllably block the FOV of each eye separately. All or some elements of vision test unit 205 may be in communication with each other and with controller 240. In some embodiments, system 200 may further include a user interface 250.

In some embodiments, one or more elements of system 200 may be included in a wearable housing configured to be worn by the patient. For example, shuttering unit 220 may be included in a glass-like element. In yet another example, eye movement tracking unit and shuttering unit 220 may be included in the wearable housing. In some embodiments, vision test unit 205 may be included in a single housing configured to be worn by the patient. In such an arrangement, eye movement tracking unit 210, screen 220 and shuttering unit 230 may all be embedded in a single housing, for example, a helmet-like housing, a hat-like housing, virtual reality glasses or the like Vision test unit 205 may be configured to communicate with controller 240 using a single communication system, for example, a single USB cable to connect vision test unit 205 to controller 240, Bluetooth transceivers or any other wired or wireless communication systems. In some embodiments, system 200 may be all included in a single housing configured to be worn by the patient. Controller 240 may be any processing unit that is configured to control the various elements of system 200. Controller 240 may include a processor 242 configured to execute instructions stored in a memory 244 associated with processor 242. Processor 242 may include any computing platform, for example, a Central Processing Unit (CPU) processor, a chip or any suitable computing or computational device. Memory 244 may include non-transitory (non-volatile) readable medium and/or non-transitory storage medium, such as for example a memory, a disk drive, or a USB flash memory for storing instructions, e.g., computer-executable instructions, which, when executed by a processor (e.g., processor 242), carry out methods disclosed herein, for example, method for diagnosing eyesight, disclosed below.

User interface 250 may be or may include input devices such as, a mouse, a keyboard, a touch screen or pad or any suitable input device that may allow a user to communicate with controller 240. User interface 250 may include a separate screen or may be in communication with screen 220 for presenting to the user data, results, recommendations or the like.

In some embodiments, eye-movement tracking unit 210, also known in the art as "eye-tracker", may be configured to track the movement of a portion of the eye, for example, the pupil. Unit 210 may include at least one sensor for sensing the movement of the eye by sensing the movement of the pupil or other portions of the eye. There are some sensors that can sense the eye-movement, for example, light sensors, usually infrared, that may measure light reflected from the eye and sensed by a video camera or other optical sensor. In yet another example, the eye movement can be sensed by electric potentials measured with electrodes placed around the eyes. The eyes are the origin of a steady electric potential field, which can also be detected in total darkness and if the eyes are closed. In some embodiments, eye-movement tracking unit 210 may be placed in proximity to the eye, for example, IR sensors (e.g., cameras) may be placed on glasses (or any other wearable device) worn by the patient, or electrodes for measuring electric potential may be placed around the patient's eyes. In some embodiments, eye-movement tracking unit 210 may be placed at a predetermined distance from the eye, for example, an IR sensor may be attached to the lower portion of screen 220 (as illustrated and discussed with respect to FIGS. 3A and 3B). Other locations may be used. Eye tracking unit 210 may send IR signals to the eye at a frequency of 50 Hz-250 Hz, for example, 230 Hz and may measure the location of the eye after each signal, for example, by measuring the IR reflection from the pupil.

Figure 3A:
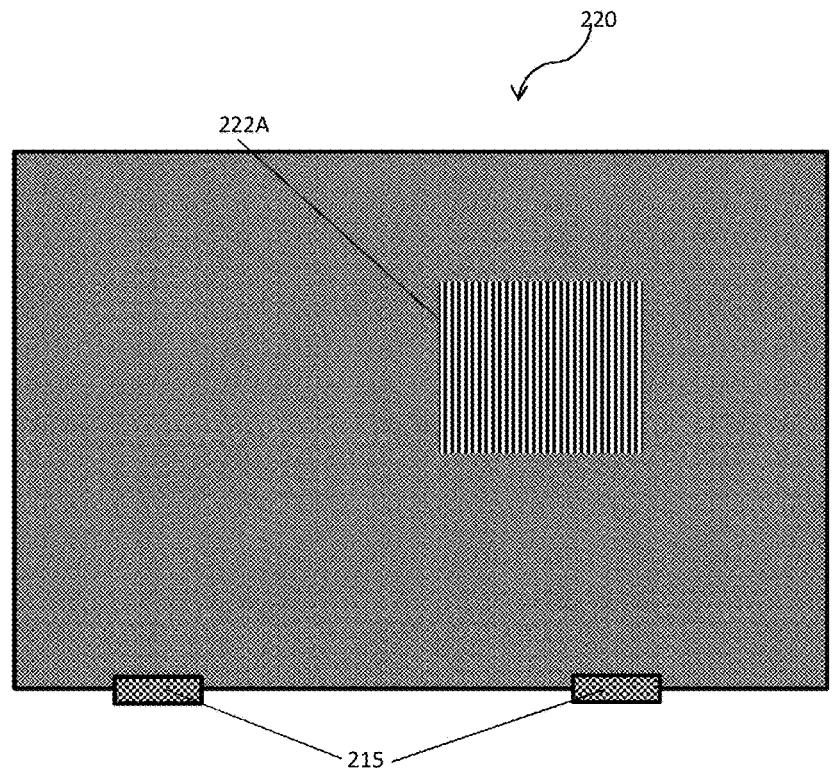
FIGS. 3A and 3B are illustrations of exemplary visual stimulations display according to some embodiments of the invention.
Figure 3B:
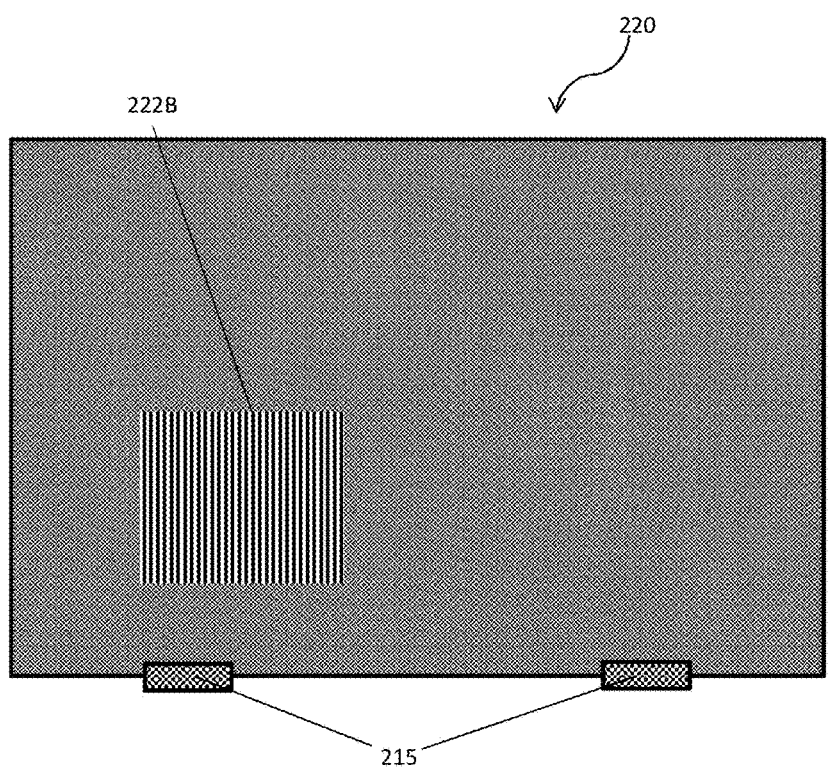

Reference is made to FIGS. 3A and 3B that are illustrations of screens for visual stimulations according to some embodiments of the invention.

Screen 220 may be any visual display known in the art that is configured to display a visual stimulation, for example, virtually represented Teller card 222A and/or 222B. Screen 220 may present visual stimulations 222A and/or 222B to the user. Screen 220 may be a touch screen, plasma screen, Light Emitting Diode (LED) screen, a medical grade display or the like. Screen 220 for visual stimulation may be a screen configured to display black and white pixels and visual stimulations 222A and/or 222B may include only black and white graphical elements. The use of black and white visual stimulation is according to the optimal contrast sensitivity of the human eye, yet different visual stimulation may be used. Screen 220 may be configured to display visual stimulation 222A and/or 222B to the user at an optical grade contrast, for example, the resolution of the screen must be higher than the highest Teller card 26.0 CPC such that the Teller card generated on the screen may have the required resolution.

The visual stimulation may include a visual stimulation (i.e., digital representation) of Teller-cards, different objects, animated objects (e.g., a dancing clown), 2D objects for simulating 3D vision (e.g., two similar objects presented to each eye at a different location), or the like. In some embodiments, screen 220 may be in communication with user interface 250. In other embodiments, user interface 250 may include a separate screen.

In some embodiments, elements of eye movement tracking unit 210, for example, sensors (e.g., IR cameras) 215, may be located in the peripheral area of screen 220, as illustrated in FIGS. 3A and 3B.

In some embodiments, vision test unit 205 may include a first screen 220 for visual stimulation of the first eye and a second screen 220 for visual stimulation of the second eye. The first and second screens 220 may be included in a single housing, such as a wearable housing, for example, in a helmet-like housing, a hat-like housing or virtual reality glasses. In some embodiments, controller 240 may be configured to display to the patient first visual stimulation 222A on first screen 220 and display to the patient second visual stimulation 222B on the second screen.

Figure 4:
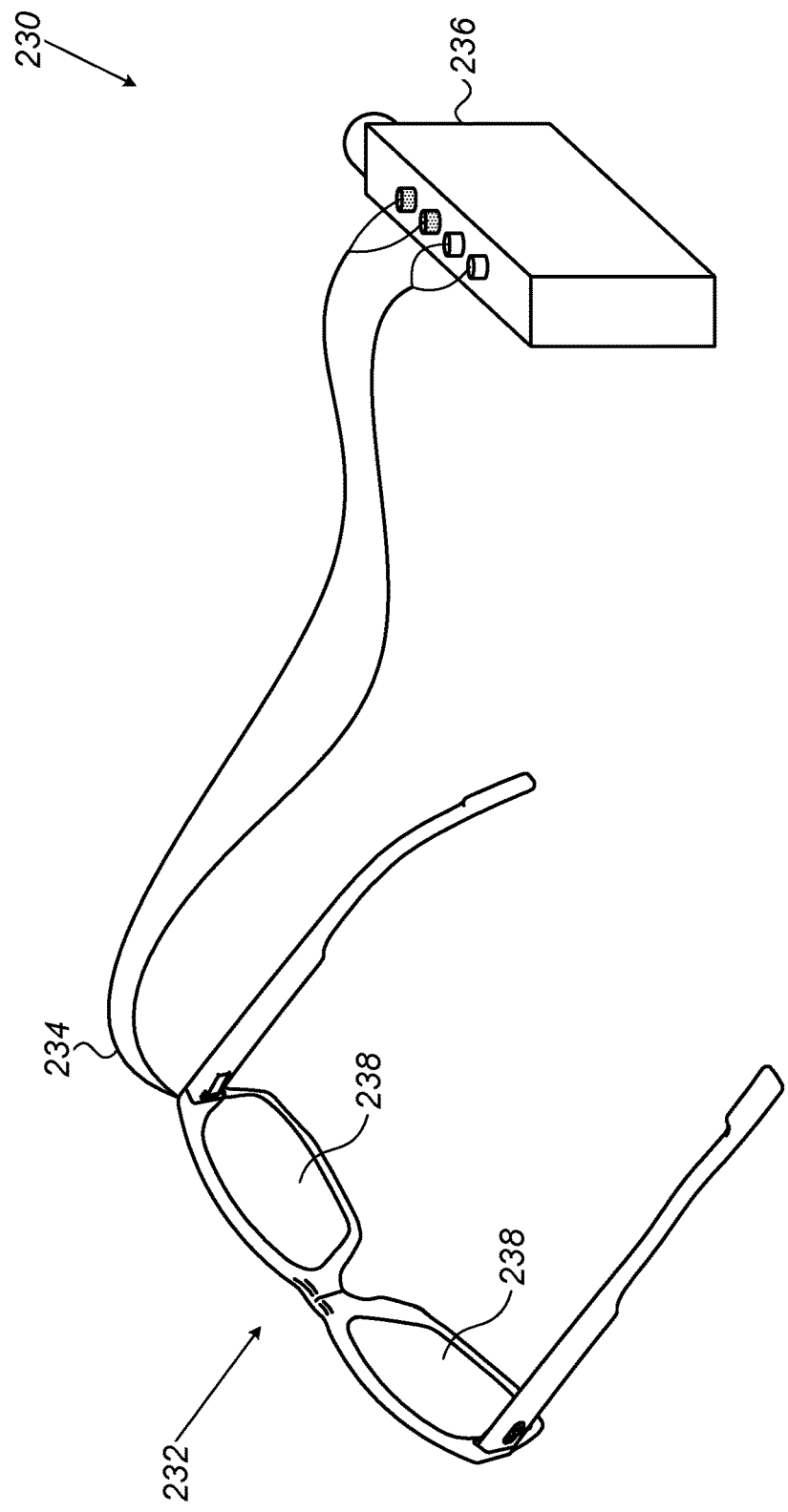
FIG. 4 is an image of an exemplary shuttering unit according to some embodiments of the invention.

Reference is made to FIG. 4 that is an illustration of shuttering unit 230 according to some embodiments of the invention. Shuttering unit 230 may be configured to block the FOV of each eye separately. Shuttering unit 230 may have a form of shuttering glasses, as illustrated in FIG. 4, or any other wearable device, for example, a helmet, a hat or a head bend having FOV blocking elements, or the like. Shuttering unit 230 may include a FOV blocking element 232, connecting elements 234 (e.g., wires or transceivers for wireless communication) and a controlling unit 236. Controlling unit 236 may be configured to communicate with controller 240, via wired or wireless communication. For example, shuttering unit 230 may be in direct wired communication via a USB port included in controller 240. In yet another example, shuttering unit 230 may include a transceiver for conducting wireless communication with controller 230, for example, via Bluetooth communication. According to some embodiments, shuttering unit 230 may be an autonomous unit in active communication with controller 240 to controllably block the FOV of an untested eye during the test of the other eye.

An exemplary shuttering unit 230 may block the FOV of each of the patient's eyes according to instructions given to shuttering unit 230 by controller 240. For example, shuttering unit 230 may block the FOV of the right eye of the patient when eye-movement tracking unit 210 is tracking the movement of the left eye of the patient. In some embodiments, shuttering unit 230 may block the FOV of the same eye which eye-movement tracking unit 210 is tracking. In some embodiments, one or more sensors of eye-movement tracking unit 210 may be located on shuttering unit 230, for example, two sensors (e.g., IR cameras) each located on the lower portion of a shuttering unit such as shuttering glasses 230 illustrated in FIG. 4, on the right and left frames, or a single sensor located on the bridge between the right and left screens covering the right and left eyes, as disclosed below.

Shuttering unit 230 may include one or more FOV blocking elements 238 each having an ability to block the FOV on command, for a predetermined period of time, for example, 0.005 second, 0.01 second, 0.1 second, 1 second, 2 seconds or the like. An exemplary FOV blocking elements 238 may include one or two 3D active Liquid Crystal Display (LCD) transparent screens configured to darken thus blocking the FOV of at least one eye of the patient. Alternatively, FOV blocking elements 238 may be or may include any other elements that may block the FOV of the eye of the patient, e.g., a covers, one or more fins or the like. The blocking frequency may be controlled to be at least, for example, 0.5 Hz-200 Hz. In some embodiment, shuttering screen(s) 238 may block Electro-Magnetic (EM) radiation in visible light spectrum from reaching the patient's eye, thus blocking the patient's FOV, but in the same time allowing EM radiation in the IR spectrum to reach the eye, for example, IR radiation from eye-movement tracking unit 210, located on the lower frame of screen 220. The frame of shuttering unit 230 may be worn as regular glasses, supported by the patient's ears, may be placed on the patient's forehead, or may be placed at any other way that may enable the one or more FOV blocking elements included in shuttering unit 230 to block the FOV of the patient's eyes.

In some embodiments, the frequency of the measurements made by eye tracking unit 210 (e.g., the frequencies of the IR signals sent and received from the eye) may be equal to or higher than the frequency of blocking the FOV of the eye by shuttering unit 230. In some embodiments, eye tracking unit 210 and shuttering unit 230 may be controlled (e.g., synchronized) such that for every cycle of FOV blocking of the first eye at least one measurement of the location of the second eye may be taken by tracking unit 210.

Figure 5:
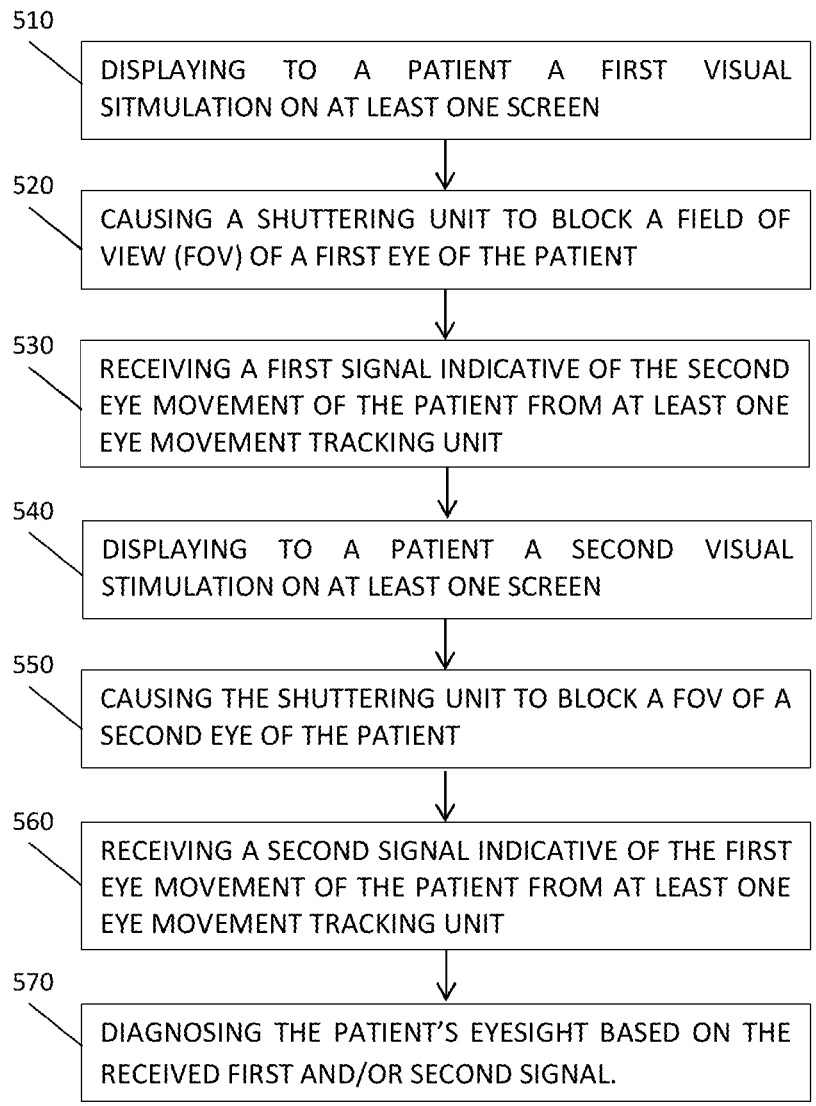
FIG. 5 is a flowchart of a method of eyesight diagnosis according to some embodiments of the invention.

Reference is now made to FIG. 5 which is a flowchart of a method of automatically diagnosing eyesight of a patient according to some embodiments of the invention. Embodiments of the method may be performed by a controller, such as, controller 240, based on instructions stored in a memory such as memory 244 and executed by processor 242. Alternatively, embodiments of the method may be performed by any other suitable controller.

In operation 510, the method may include displaying to a patient a first visual stimulation (e.g., visual stimulation 222A) on at least one screen (e.g., screen 220). The first visual stimulation may be displayed in a first location on screen 220. The first visual stimulation may include a black and with image, for example, a Teller card as illustrated in FIGS. 3A and 3B. The first visual stimulation may have a first predefined contrast sensitivity level, for example, a number of CPC of a Teller card that is correlative to an acuity level. A contrast sensitivity level of a visual stimulation, as used herein, corresponds to the size of contrasted details (e.g., strips having either black or white color) of a particular visual stimulation. The size may include the width and length of a 2D image, the width and length and height of a 3D image, the size of the contrasted details within the image or the like. For example, the contrast sensitivity of a Teller card is determined by the width and the density of the black and white strips. The Teller card may have a square shape having known dimensions (with respect to the size of the screen presenting the Teller card).

In operation 520, the method may include causing a shuttering unit (e.g., shuttering unit 230) to block the FOV of a first eye of the patient while unblocking the FOV of a second eye. Controller 240 may control a first shuttering screen 238 to block the FOV of the first eye. In operation 530, the method may include receiving a first signal indicative of the second eye movement of the patient from at least one eye movement tracking unit (e.g., tracking unit 210). The second eye may be drawn to gaze or look at the first stimulation displayed and this movement of the eye may be track by eye tracking unit 210. If the first stimulation has contrast sensitivity level that can be detected by the eye of the patient (e.g., the patient sees the contrasted details of the visual stimulation) the unblocked eye of the patient may be drawn to look at visual stimulation. Such a movement of the eye may be detected by eye movement tracking unit 210 and sent as signal to controller 240.

In some embodiments, the method may include displaying an animated image or any other image (e.g., dancing clown) to the patient before and/or after displaying visual stimulation 222A or 222B. The image may be displayed in order to capture the attention of the patient during the test. The image may be displayed at the center of screen 220 or in any other location on screen 220. In some embodiments, the location of the image may be different from the first location of first visual stimulation 222A. The image may be displaying when the FOV of both eyes is open, or when the FOV of one eye is blocked. In some embodiments, when the image disappears from screen 220 and first visual stimulation 222A appear on screen 220 at a first location, the second eye of the patient may be drawn to follow first visual stimulation 222A to the first location on screen 220. This movement of the second eye may be detected by eye movement tracking unit 210.

In operation 540, some embodiments of the method may include displaying to the patient a second visual stimulation 222B on the at least one screen 220. The second visual stimulation may have a second known contrast sensitivity level, for example, a known number of CPC of a Teller card that is correlative to an acuity level. The second visual stimulation may have the same contrast sensitivity level as the first visual stimulation or may have different one. The second visual stimulation may be located at a second location on screen 220, different from the first location. In some embodiments, system 200 for eyesight diagnosis may include two screens 220, each one placed in front of a single eye, for example, the screens may be included in virtual reality-like glasses, and controller 240 may control each screen separately. For example, controller 240 may display to the patient the first visual stimulation on first screen 220 and display to the patient the second visual stimulation on a second screen 220. In some embodiments, controller 240 may display an image (e.g., an animated image) before and/or after displaying the second visual stimulation.

In operation 550, some embodiments of the method may include causing the shuttering unit (e.g., unit 230) to block the FOV of the second eye of the patient, while unblocking the FOV of the first eye.

As may be seen in operation 560, some embodiments of the method may include receiving a second signal indicative of the first eye movement of the patient from the at least one eye movement tracking unit (e.g., tracking unit 210). When the second visual stimulation has contrast sensitivity level that can be detected by the eye of the patient (e.g., the patient sees the contrasted visual stimulation) the unblocked first eye of the patient may be drawn to look at the second visual stimulation, such a fine movement of the first eye may be detected by eye movement tracking unit 210 and sent as signal to controller 240.

In operation 570, embodiments of the method may include diagnosing the patient's eyesight based on the received first and/or second signals. Controller 240, may receive the first signal indicative of the second eye movement of the patient caused by the presentation of the first visual stimulation and blocking the FOV of the first eye and may compare the signal to a first reference signal stored in a lookup table, for example, in a memory associated with controller 240 (e.g., memory 244). The reference signals stored in the memory may each be associated with a healthy eye movement in response to a display of a specific visual stimulation (having a specific contrast sensitivity level and a specific location on the screen) of either the first or the second eyes. If the first visual stimulation displayed to the patient was detected by the second eye of the patient (the patient successfully noticed the visual stimulation presented on the screen) and a corresponding movement was detected by the eye tracking unit, the signal received may be compared to the stored reference signal. If the comparison yields that the signals are substantially the same, controller 240 may diagnose that the second eye of the patient can see the first visual stimulation. If the received signal is substantially different from the stored reference signal, or that no significant movement of the eye was detected, controller 240 may diagnose that the second eye of the patient may have an acute problem. The diagnosed problem may be correlated to the specific contrast sensitivity level (e.g., acuity level) of the first visual stimulation.

In some embodiments, the controller may perform a similar diagnosis to the second signal indicative of the first eye movement of the patient. The second signal may be received during the presentation of the second visual stimulation and blocking the FOV of the second eye. The second signal may be compared to a second reference signal similarly to the above. In some embodiments, the reference signals may be received from previous tests conducted on healthy testees, may be calculated using a computer simulation, stored for a specific patient in the past tests or the like.

In some embodiments, the method may further include calibration of the system. A plurality of animated objects (e.g., moving dots) may be presented to the patient on screen 220. Tracking unit 210 may track the movement of both the right and left eyes, looking for example, for IR reflections to determine the location of each pupil with respect to tracking unit 210. The calibration process may be conducted before operation 510 or at any point during the test if necessary.

In some embodiments, controller 240 may perform and/or repeat operations 510-570 at any order. In some embodiments, controller 240 may display various visual stimulations according to a predetermined sequence, for example, display some of the Teller cards from the 0.5 CPD to the 32 CPD or objects in a decreasing size order. Controller 240 may be configured to correlate each of the received signals indicative of the eye movement with the specific visual stimulation that was presented to the patient during measurement of the eye movement.

In some embodiments, system 100 may measure phoria (e.g., the central focal point of each eye). The system may calculate the gazing location, which is the point on screen 220 to which the pupil of each eye is looking when the FOV of one eye is blocked by unit 230, with respect to the location of a visual stimulation presented on screen 220. For a patient having a healthy eye sight the gazing location and the location of the visual stimulation (e.g., a visual stimulation having a shape of a small circle) may be substantially the same. When the gazing location and the location of the visual stimulation are not the same, controller 240 may calculate the distance between the gazing location and the location of the visual stimulation. Knowing the distance of screen 220 from the patient's eyes, controller 240 may calculate the phoria level (e.g., squint) of each eye, for example, if the measured distance between the gazing location and the location of the visual stimulation is 4 cm (measured in number of pixels on screen 220) and the distance between screen 220 and the patient's eyes is 50 cm, the measured phoria may be 8 cm/1 meter (also known in the art as 8 ESO).

In some embodiments, system 100 may diagnose Amblyopia problems. In patient suffering from Amblyopia vision loss occurs because nerve pathways between the brain and the eye aren't properly stimulated causing the brain to ignore stimulation from one (and sometimes even both) of the eyes. In some embodiments, controller 240 may be configured to present to each eye a specific visual stimulation at a specific location on the screen and compare between the gazing directions of both eyes looking simultaneously at the same visual stimulation, using tracking unit 210. For example, a one year old baby with healthy eye sight may have the ability to see the resolution of a Teller card having 13 CPC in both eyes in order to be diagnosed as one not having an Amblyopia problem. At age 4 and above healthy eyesight of a patient may be determined as having the ability to see the resolution of a Teller card having 26 CPC in both eyes. In some embodiments, the specific location may be in the middle of the screen and the screen may be placed at a distance of 55-65 cm. from the patient's eyes.

In some embodiments, system 100 may diagnose 3D vision problems of the patient. Controller 240 may be configured to alternately display on screen 220 a first and a second identical 2D visual stimulations located at a known distance from each other. During the displaying of the first 2D visual stimulation for example, on the right side of screen 220, controller 240 may, cause shuttering unit 230 to block the FOV of a first eye (e.g., the left eye) and vice versa. By alternating the displaying of the first and second 2D visual stimulations and correspondingly blocking of the FOV of the first and second eyes, system 100 may cause the patient to see a 3D image. The alternate displaying of the visual stimulations and the blocking of the FOV of the right and left eyes may be conducted at the same frequency, for example, at a frequency of 120 Hz.

Controller 240 may receive from tracking unit 210 signals indicative of the movement of both the left and right eyes during the presentation of the alternating first and second visual stimulations. Eye tracking unit 210 may detect if the patient's eyes are gazing to the same location (e.g., a point located between the first and second 2D visual stimulations), which means that the patient's brain is creating a 3D object from the alternating 2D visual stimulations. If the patient's eyes are not gazing to the same location, the controller may conclude that the patient's brain didn't create the 3D object, thus may diagnose a problem in the 3D vision of the patient.

According to some embodiments, controller 240 may select the distance between the first and the second visual stimulation according to characteristics of the tested patient, a predetermined program selected for the particular patient (e.g., patients at different ages may be expected to create 3D object from 2D images placed at a different minimal distances). According to some embodiments controller 240 may change the distance between the first and the second visual stimulation during the test in order to diagnose the 3D vision of the patient. The closer the first and the second visual stimulations that caused the patient's eyes to gaze to the same direction, the better is the patient's 3D vision.

In some embodiments, system 100 may diagnose pathologies in the patient's eyes. For example, system 100 may further include an optical camera and a source of bright light beam (e.g., a Retinoscope) that sends to the eyes strong bright light beam focused towards the pupil (e.g., a light flash). The camera may detect if the reflections from the pupil of the eyes have different wavelengths (e.g., colors). Change in the color of the reflections (e.g., from red to white) may be indicative of a pathology in the eye (e.g., a tumor). In yet another example, system 100 may measure the diameter of each pupil based on signals received from eye tracking unit 210. A difference in the diameter between the right and left eyes may further indicate a suspected pathology in at least one of the eyes. In yet another example, the size and shape of the pupil of each eye may be measured by system 100 based on signals received from eye tracking unit 210. If one of the pupils is not a complete circle it may indicate that the patient's suffers from an eyelid drop.

The following are some exemplary processes for detecting deviation from healthy eye behavior according to some embodiments of the invention. The processes may be performed using system 200.

Measuring Phoria—the Central Focal Point of Each Eye.
1) Controller 240 may display for example, an animated object at the center of screen 220.
2) Shuttering unit 230 may block the FOV of the right eye for 2 seconds, during which eye-movement tracking unit 210 may tract the location of the right eye pupil (the blocked eye) and the gazing direction of the pupil of the left eye towards the animated object.
3) Shuttering unit 230 may unblock the FOV of both eyes for 2 seconds while measuring the movements of both the left and right eyes.
4) Shuttering unit 230 may block the FOV of the left eye for 2 seconds, during which eye-movement tracking unit 210 may tract the location of the pupil of the left eye and the gazing direction of the pupil of the right eye towards the animated object.
5) Repeating the stages until detecting a focal point of each eye.

Measuring Eye-Acuity May Include:
1) Conducting a calibration process by displaying 6 moving points to the patient and detecting by eye tracking unit 210 the location of the pupil of each eye.
2) Presenting to the patient an animated image for grabbing the attention of the patient.

During steps 3-16 eye movement tracking unit 210 may track and records the movement of each of the left and right eyes.
3) Presenting a 3.2 CPC Teller card on screen 220 at a first location while blocking the FOV of the right eye for 4 seconds.
4) Presenting a 3.2 CPC Teller card on screen 220 at a first location while blocking the FOV of the left eye for 4 seconds.
5) Presenting an animated image when the FOV of both eyes is unblocked.
6) Presenting a 6.5 CPC Teller card on screen 220 at a first location while blocking the FOV of the right eye for 4 seconds.
7) Presenting a 6.5 CPC Teller card on screen 220 at a second location while blocking the FOV of the right eye for 4 seconds.

8) Presenting an animated image when the FOV of both eyes is unblocked.
9) Presenting a 6.5 CPC Teller card on screen 220 at the first location while blocking the FOV of the left eye for 4 seconds.
10) Presenting a 6.5 CPC Teller card on screen 220 at the second location while blocking the FOV of the left eye for 4 seconds.
11) Presenting an animated image when the FOV of both eyes is unblocked.
12) Presenting a 13 CPC Teller card on screen 220 at a first location while blocking the FOV of the right eye for 4 seconds.
13) Presenting a 13 CPC Teller card on screen 220 at a second location while blocking the FOV of the right eye for 4 seconds.
14) Presenting an animated image when the FOV of both eyes is unblocked.
15) Presenting a 13 CPC Teller card on screen 220 at the first location while blocking the FOV of the left eye for 4 seconds.
16) Presenting a 13 CPC Teller card on screen 220 at the second location while blocking the FOV of the left eye for 4 seconds.
17) Determining which of the presented Teller card was detected by each of the eyes.
18) Diagnosing the acuity based of the determined.

Measuring 3D Vision May Include:
Controlling shuttering unit 230 to alternately block the FOV of the left and right eyes at a frequency of 120 Hz.
1) Presenting on screen 220 a first visual stimulation while blocking the FOV the right eye;
2) Presenting on screen 220 a second visual stimulation, identical to the first visual stimulation at a known distance to right from the first visual stimulation while blocking the FOV the left eye;
3) Alternately repeating steps 1) and 2) while tracking using tracking unit 210 the gazing direction of both the right and left eyes;
4) Determining if both the left and right eyes are gazing (looking) at substantially the same location (e.g., point on screen) to determine a 3D vision.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:
1. A system for eyesight diagnosis, comprising:
a vision test unit, comprising:
at least one eye movement tracking unit configured to track the movement of a portion of the eye;
at least one screen for visual stimulation; and
a shuttering unit configured to controllably block the field of view (FOV) of each eye separately; and
a controller configured to:
display to a patient a first visual stimulation on the at least one screen;
cause the shuttering unit to block the FOV of a first eye of the patient while unblocking the FOV of a second eye;
receive a first signal indicative of the second eye movement of the patient from the at least one eye movement tracking unit; and
diagnose the patient's eyesight based on the received first signal.

2. The system for eyesight diagnosis of claim 1, wherein the controller is further configured to:
display to the patient a second visual stimulation on the at least one screen;
cause the shuttering unit to block the FOV of the second eye of the patient, while unblocking the FOV of the first eye;
receive a second signal indicative of the first eye movement of the patient from the at least one eye movement tracking unit; and
diagnose the patient's eyesight based on the received second signal.

3. The system for eyesight diagnosis of claim 2, further comprising:
a first screen for visual stimulation of the first eye; and
a second screen for visual stimulation of the second eye, and
wherein the controller is configured to
display to the patient the first visual stimulation on the first screen; and
display to the patient the second visual stimulation on the second screen.

4. The system for eyesight diagnosis of claim 2, wherein the controller is configured to:
display the first visual stimulation in a first location on the screen;
display the second visual stimulation in a second location on the screen, different from the first location.

5. The system for eyesight diagnosis according to claim 2, wherein the first and second visual stimulations are identical images located at a predetermined distance from each other, and
wherein the controller is further configured to:
alternately display the first and second identical visual stimulations while alternately causing the shuttering unit to block the FOV of the first and second eyes of the patient; and
determine if both the first eye and the second eye gaze to the same location on the at least one screen.

6. The system for eyesight diagnosis of claim 1, wherein the signal indicative of the eye movement is received from a camera included in the at least one eye movement tracking unit, that detects infrared reflections from the pupil of the eye.

7. The system for eyesight diagnosis of claim 1, wherein the signal indicative of the eye movement is received from at least one electrode placed close to the eye.

8. The system for eyesight diagnosis of claim 1, wherein the screen for visual stimulation is a screen configured to display black and white pixels.

9. The system for eyesight diagnosis of claim 1, wherein the controller is further configured to display to the patient an animated image.

10. The system for eyesight diagnosis of claim 1, wherein the vision test unit is included in a single housing configured to be worn by the patient.

11. The system for eyesight diagnosis of claim 1, wherein sensors included in the at least one eye movement tracking unit are located on the peripheral area of the screen.

12. The system for eyesight diagnosis of claim 1, wherein the shuttering unit is shuttering glasses configured to controllably shutter the FOV of each lens separately.

13. The system for eyesight diagnosis of claim 1, wherein the controller is further configured to diagnose pathologies in at least one eye of the patient based on the signals received from the eye tracking unit.

14. The system for eyesight diagnosis of claim 1, further comprising:
a camera; and
a source of a bright light beam,
and wherein the controller is further configured to diagnose pathologies in at least one eye of the patient based on the signals received from the camera.

15. A controller for controlling a system for eyesight diagnosis, comprising:
a processor; and
a non-volatile memory that store thereon instructions that when executed by the processor cause the controller to:
display to a patient a first visual stimulation on at least one screen;
cause a shuttering unit to block a field of view (FOV) of a first eye of the patient while unblocking the FOV of a second eye;
receive a first signal indicative of the second eye movement of the patient from at least one eye movement tracking unit; and
diagnose the patient's eyesight based on the received first signal.

16. The controller for controlling a system for eyesight diagnosis of claim 15, wherein the instructions further cause the controller to:
display to the patient a second visual stimulation on the at least one screen;
cause the shuttering unit to block the FOV of the second eye of the patient, while unblocking the FOV of the first eye;
receive a second signal indicative of the first eye movement of the patient from the at least one eye movement tracking unit; and
diagnose the patient's eyesight based on the received second signal.

17. A method, to be executed by a controller, for eyesight diagnosis, comprising:
displaying to a patient a first visual stimulation on at least one screen;
causing a shuttering unit to block a field of view (FOV) of a first eye of the patient while unblocking the FOV of a second eye;
receiving a first signal indicative of the second eye movement of the patient from at least one eye movement tracking unit; and
diagnosing the patient's eyesight based on the received first signal.

18. The method of claim 17, comprising:
displaying to the patient a second visual stimulation on the at least one screen;
causing the shuttering unit to block the FOV of the second eye of the patient, while unblocking the FOV of the first eye;
receiving a second signal indicative of the first eye movement of the patient from the at least one eye movement tracking unit; and
diagnosing the patient's eyesight based on the received second signal.

19. The method of claim 18, comprising:
displaying to the patient the first visual stimulation on a first screen; and
displaying to the patient the second visual stimulation on a second screen.

20. The method of claim 18, comprising:
displaying the first visual stimulation in a first location on the screen;
displaying the second visual stimulation in a second location on the screen, different from the first location.

* * * * *